United States Patent [19]

Jeng et al.

[11] Patent Number: 5,064,541

[45] Date of Patent: * Nov. 12, 1991

[54] DEVICES AND METHODS FOR THE COLLECTION OF A PREDETERMINED VOLUME OF PLASMA OR SERUM

[75] Inventors: Tzyy-Wen Jeng, Vernon Hills; Kristin D. Elmore, Waukegan; Gary M. Oosta, Gurnee; Terry A. Pry, Libertyville, all of Ill.

[73] Assignee: Abbott Laboratories, Abbott Park, Ill.

[*] Notice: The portion of the term of this patent subsequent to Jun. 12, 2007 has been disclaimed.

[21] Appl. No.: 499,864

[22] Filed: Mar. 27, 1990

Related U.S. Application Data

[63] Continuation-in-part of Ser. No. 335,064, Apr. 7, 1989, Pat. No. 4,933,092.

[51] Int. Cl.$^5$ .................. B01D 37/00; B01D 39/14
[52] U.S. Cl. .................. 210/767; 210/295; 210/502.1; 210/510.1; 210/806; 422/100; 422/101; 436/177
[58] Field of Search .............. 210/206, 259, 295, 314, 210/323.1, 335, 502.1, 510.1, 651, 702, 729, 730, 732, 782, 789, 806, 767; 435/2; 422/101, 56, 100; 436/177, 178, 808

[56] References Cited

U.S. PATENT DOCUMENTS

| | | | |
|---|---|---|---|
| 3,888,629 | 6/1975 | Bagshawe | 436/804 |
| 3,891,553 | 6/1975 | Ayres | 210/789 |
| 3,902,964 | 9/1975 | Greenspan | 436/177 |
| 3,960,727 | 6/1976 | Hochstrasser | 210/782 |
| 4,464,254 | 8/1984 | Dojki et al. | 210/516 |
| 4,477,575 | 10/1984 | Vogel et al. | 210/767 |
| 4,594,327 | 6/1986 | Zuk | 422/56 |
| 4,753,776 | 6/1988 | Hillman et al. | 422/101 |
| 4,820,644 | 4/1989 | Schäfer et al. | 422/101 |
| 4,933,092 | 6/1990 | Aunet et al. | 210/729 |

Primary Examiner—W. Gary Jones
Attorney, Agent, or Firm—Frank S. Ungemach; Daniel R. Curry

[57] ABSTRACT

A device and method for permitting the separation of plasma or serum from whole blood. The device comprises a matrix of hydrophilic sintered porous material to which at least one red blood cell agglutinating agent has been applied. According to a first method of using the device, a sample of whole blood is applied to a first end of the matrix and the red blood cells within the sample come in contact with the agglutinating agents present in the matrix. The blood cells agglutinate, and are entrapped in the interstices of the matrix, while substantially blood-cell-free serum or plasma accumulates near the outlet of the device. A filter means in liquid receiving relationship with the matrix functions to wick the serum of plasma from the matrix.

According to an alternative aspect of the invention, a filter means in liquid receiving relationship with the outlet of the matrix functions to retain any blood cells which pass through the matrix as the filter means wicks the plasma or serum from the matrix. Additional agglutinating agents may be incorporated within the filter means to facilitate retention of blood cells which pass through the matrix.

Another aspect of the present invention involves a device for the measurement of a serum or plasma sample, utilizing a matrix of sintered porous material, such as sintered glass, sintered steel, sintered ceramics, sintered plastics, and equivalents thereof. The matrix is characterized by a reproducible fluid uptake capacity proportional to the fixed dimensions of said matrix, a minimal reactivity with plasma or serum components, and a hydrophilic internal surface which enables the matrix to collect and retain a predetermined volume of sample for analysis.

20 Claims, 2 Drawing Sheets

DEVICES AND METHODS FOR THE COLLECTION OF A PREDETERMINED VOLUME OF PLASMA OR SERUM

This application is a continuation in-part of U.S. patent application Ser. No. 335,064 filed Apr. 7, 1989, now U.S. Pat. No. 4,933,092.

BACKGROUND OF THE INVENTION

1. Field of the Invention

The present invention relates generally to methods for separating plasma or serum from whole blood. More particularly, the invention relates to devices capable of separating plasma or serum from whole blood comprising a hydrophilic sintered porous material in which at least one red blood cell agglutinating agent has been incorporated. Agglutinated blood cells are removed from whole blood by the sieving action of the matrix of the sintered porous material, and optional additional filter means.

The present invention also relates to devices and methods for collecting a predetermined amount of a plasma or serum sample for analysis in a diagnostic assay. More particularly, the invention relates to a matrix of sintered porous material, wherein the matrix provides a reproducible fluid uptake capacity.

2. Background

Modern clinical diagnostic methods are routinely carried out on blood samples. Unfortunately, red blood cells present in whole blood scatter and absorb light thus interfering with assay methodologies which measure either reflected or transmitted light. Other cells may interfere with particular determinations; for example, cholesterol determinations can be affected by cholesterol present in cell membranes. For this reason, many assay methodologies are carried out on plasma or serum which must be separated from a whole blood sample.

Centrifugation is a well known method in the art by which plasma (before clotting) and serum (after clotting) is separated from whole blood. Stratifying whole blood by centrifugation, however, is time consuming and requires cumbersome laboratory equipment. The use of red blood cell agglutinating agents such as those disclosed in Van Oss, et al., *Vox. Sang.*, vol. 34, pp 351-361 (1978) can be helpful in carrying out centrifugation and other red blood cell separation techniques.

Dojki, et al., U.S. Pat. No. 4,464,254, issued Aug. 7, 1984, disclose a piston device capable of isolating serum from an already stratified blood sample. The device consists of a piston head connected to an open-ended sampling tube. The piston head is composed of a one-way valve under which is located a cavity containing a porous plastic filter body. Insertion of the piston head-sampling tube assembly into a test tube containing a stratified sample of blood allows serum to pass through the filter body and valve into the interior of the sampling tube. The volume and purity of the serum which can be separated from the whole blood is contingent upon the completeness of the stratification of the blood.

Vogel, et al., U.S Pat. No. 4,477,575, issued Oct. 16, 1984, disclose a device and a process using the device to separate serum from whole blood by causing whole blood to pass into and through a layer of glass fibers with diameters from 0.2 to 5 microns and with a density of 0.1 to 0.5 g/cm$^3$. The volume of plasma or serum which can be separated from whole blood by this device is disclosed to be less than 50% of the absorption volume of the glass fiber layer.

Zuk, U.S. Pat. No. 4,594,327, issued June 10, 1986, discloses an analytical method wherein a whole blood sample is combined with a red blood cell binding agent and the mixture is then filtered through a solid bibulous element to which is bound at least one specific binding pair member so as to remove the agglutinated red blood cells. The patent discloses anti-red blood cell antibodies, polymeric amino acids, such as polylysine, and lectins, such as wheat germ agglutinin, as suitable red blood cell binding agents for causing the aggregation of red blood cells in whole blood.

Hillman, et al., U.S. Pat. No. 4,753,776, issued June 28, 1988, disclose a device and a process using the device to separate serum from whole blood using capillary action to pass whole blood through a glass microfiber filter. The patent discloses an alternative embodiment in which whole blood is passed through a filter to which red blood cell agglutinins have been attached. Rather than retaining the red blood cells, however, the filter disclosed merely retards their flow, eventually allowing their escape.

Trasch, et al., EPO Publication No. 133,895, published Mar. 13, 1985, disclose a red blood cell retaining substrate and a process using the substrate for retaining red blood cells on filters thus allowing the recovery of plasma from whole blood. The red blood cell retaining substrates of the invention are stated to induce coagulation, but not hemolysis, so that the coagulated corpuscular components can be removed on a filter, while the plasma passes through. The publication discloses alternative embodiments where the retaining substrate is incorporated into the filter or into a pre-filter layer. The publication states that absorptive, porous, liquid permeable carriers or filters, in the form of paper, fleece, gel or tissues, comprised of cellulose, wool, glass fiber, asbestos, synthetic fibers, polymers or mixtures of the same, can be used as the absorptive materials for the retaining zone.

Most portable technigues for the separation of serum or plasma are limited with respect to speed and serum yield efficiency. Blood separation devices utilizing glass fiber membranes, for example, tend to separate serum at a relatively slow speed and tend to retain significant quantities of serum or plasma in the interstices of the membrane. Accordingly, there exists a desire in the art for improved devices providing rapid and efficient methods for serum and plasma separation.

Another difficulty encountered in the testing of blood samples is that it is generally necessary to measure a precise test sample volume of plasma or serum for use in diagnostic assays. This need for precision is typically met by having a trained technician use a sophisticated pipetting apparatus or by the use of expensive automated instruments. There are also test strip devices which use membrane or paper matrices to collect a plasma sample and transport that sample to a reaction zone on the test strip. Test strip devices, however, typically provide only that sample volume capacity which is needed to transport sample by capillary action through the strip to the reaction zone, and therefore a low level of precision is reguired. In test strips devices, the plasma recipient member only collects that amount of sample necessary to fill the strip which in turn ends the migration of the sample through the strip because the drawing force which causes sample subject to analysis in a test strip device is limited to that amount which passes through a defined detection zone on the test strip before the strip is filled.

SUMMARY OF THE INVENTION

The present invention relates to improved methods, devices and kits for separating plasma or serum from whole blood. Specifically, the devices of the invention comprise a matrix of hydrophilic sintered porous material in which at least one red blood cell agglutinating agent has been incorporated. The matrix is further characterized by a pore size selected such that individual blood cells will pass through the matrix but wherein agglutinated blood cells will be retained by the matrix. The devices are capable of carrying out a rapid separation of serum or plasma from whole blood while retaining only minimal quantities of serum or plasma within the interstices of the matrix.

According to one aspect of the invention, the device comprises a matrix of hydrophilic sintered porous material in which at least one red blood cell agglutinating agent has been incorporated. A sample of whole blood is applied to an inlet of the matrix and the blood cells within the sample come in contact with the agglutinating agents present in the matrix. The blood cells agglutinate and are entrapped in the interstices near the inlet of the matrix, while substantially blood-cell free serum or plasma accumulates near an outlet of the matrix. A receiving means, including materials such as filter paper or additional porous matrices, may be incorporated in liquid receiving relationship with the outlet of the matrix. The receiving means functions to wick the substantially blood-cell free serum or plasma from the outlet of the matrix, thus making the serum or plasma available for analysis or other purposes.

According to an alternative aspect of the invention, a filter means is incorporated in liquid receiving relationship with the outlet of the matrix for improved efficiency and more rapid separation of the blood cells from a sample of whole blood. The filter means may have at least one red blood cell agglutinating agent incorporated therein in order to assist in retaining the blood cells. The invention also provides methods and devices for the analysis of selected components of blood plasma or serum comprising the first porous matrix of the invention in combination with additional matrices or filter means in which analytical reagents selected for reaction with the selected components may be incorporated.

As indicated previously, removal of red blood cells is of particular interest in visually red assays. Nevertheless, removal of other blood cells is desirable as well, and is to be understood when the term "red blood cell" is employed herein in the context of retention in the matrix or removal of whole blood.

The present invention also relates to devices and methods for the collection of a predetermined volume of plasma or serum test samples using a matrix of sintered porous material that is characterized by a reproducible fluid uptake capacity proportional to the fixed dimensions of said matrix, a minimal reactivity with plasma or serum components, and a hydrophilic internal surface, wherein the matrix is encased in a housing means whereby an entry port to the matrix is defined. These characteristics enable the matrix to collect and retain a predetermined volume of sample for analysis. Optionally, an exit port from the matrix is also defined by the encasement means.

The sintered porous materials used to make the collection matrix devices of the present invention include sintered glass, sintered steel, sintered ceramics, sintered plastics and equivalents thereof. A particularly preferred material is polyethylene.

The collection matrix can optionally be used in conjunction with a blood separator means which separates plasma or serum from a whole blood sample. Typically, the matrix is in liquid receiving relationship with the blood separator means, and the matrix thereby collects a predetermined volume of plasma or serum from the blood separator means. The collection matrix can also be used in conjunction with a sample receiver means to which the matrix transfers the predetermined volume of sample for analysis. Alternatively, the analysis can be performed upon the plasma or serum sample in the matrix itself.

Suitable sample receiver means include reaction or detection vessels, such as cuvettes, test tubes, slides and reaction wells. The sample is eluted into the detection vessel by the application of an eluting buffer to the matrix. Other sample receiver means include absorbent solid phase materials having a pore size selected to induce the flow of sample from the matrix into the absorbent by capillary action. The sample receiver means can optionally include one or more analytical reagents which are reconstituted upon the transfer of test sample to the receiver means.

The collection of a serum or plasma sample for analysis is performed by applying a quantity of serum or plasma to the collection matrix and thereby collecting a predetermined volume of plasma or serum.

DETAILED DESCRIPTION OF THE INVENTION

Figure 1:
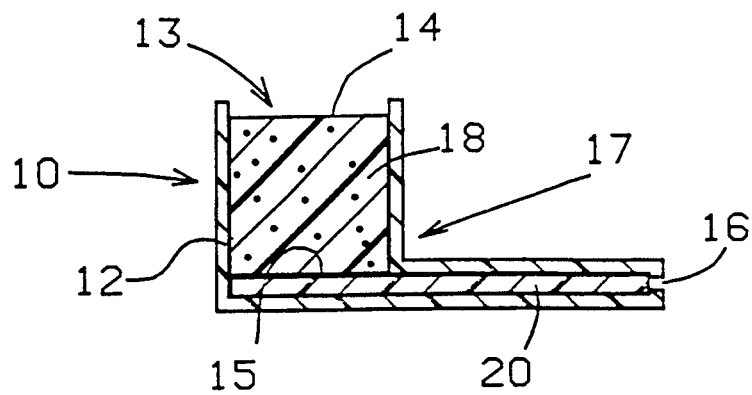
FIG. 1 is a depiction of a device comprising a porous matrix and a filter paper receiving matrix.

The present invention provides improved devices and methods for using those devices to separate plasma or serum from whole blood. The devices of the invention comprise matrices of hydrophilic sintered porous materials in which at least one red blood cell agglutinating agent has been incorporated. The matrix is characterized by a pore size such that individual blood cells will pass through it, but wherein agglutinated cells will be retained by the matrix. The devices are capable of performing rapid separations of serum or plasma from whole blood while retaining only minimal residual quantities of serum or plasma within the interstices of the porous material.

Among the materials contemplated as being suitable for the matrices of the present invention are sintered glass, sintered steel, sintered ceramics, and sintered polymers of plastic, with the preferred material being that known as sintered polyethylene such as that described in British patent No. 2,186,205. Sintered polyethylene matrices commercially available from Porex, Inc., Fairburn, Ga. or General Polymeric Corp., West Reading, Pa. may be obtained which have a pore size of from about 10 microns to about 70 microns. Such a pore size allows individual red blood cells to pass through the matrix, but retains agglutinated red blood cells within the matrix.

The matrices of the present invention are hydrophilic so as to promote the flow of aqueous liquids through them. Commercially available matrices may be either hydrophilic or hydrophobic in nature. Hydrophobic matrices may be rendered hydrophilic by a variety of known methods. Among those methods available are plasma treatment or surfactant treatment of the matrix. Plasma treatment involves exposing the hydrophobic matrix to charged gas (plasma) wherein an electronic charge is imparted to the solid surface rendering the surface wettable. Surfactant treatment involves dipping the hydrophobic matrix in a surfactant and letting it dry. This treatment assists in wetting the surface and interior of the matrix and results in the promotion of aqueous liquid flow through the matrix. It is contemplated that a wide variety of commercially available surfactant materials would be appropriate for use with the present invention. In the assays discussed in the Examples below, commercially available matrices which had been co-molded with surfactant were used and are preferred over matrices dipped in commercially available surfactants.

In general, surfactants should be selected which are compatible with the reactants or reagents placed within the matrix so as not to interfere with the preferred activity. Additionally, it should be noted that no surfactant should be present in such concentrations as to cause hemolysis of the red blood cells. In addition, care must be exercised to avoid hemodilution of the plasma sample. Hemodilution is the extraction into the plasma of the internal fluid of the red blood cell due to hypertonic conditions.

The incorporation of anti-coagulants into whole blood samples is particularly preferred for promoting the flow of plasma through the devices. Anti-coagulants mixed with the blood before application to the device prevent the blood from clotting. Separation of blood cells from a blood sample treated with anti coagulants produces plasma. Separation of red blood cells from a clotted blood sample produces serum. It is further contemplated that these anti-coagulants may be incorporated into the matrices to prevent the blood sample from clotting when applied to the device. For example, a drop of blood from a finger stick may be directly applied to the device such that anti coagulants incorporated within the device come in contact with the blood and prevent the blood from clotting. Alternatively, blood can be collected in a capillary tube previously treated with anticoagulant, and transferred to the device in this manner. Preferred anti coagulant materials include heparin, EDTA and citrate.

According to the invention, red blood cell agglutinating agents are incorporated into the porous matrices. Agglutinating agents are substances which cause individual red blood cells to adhere to one another to form clumps. It is contemplated that the agglutinating agents may be incorporated into a matrix by means such as adsorption, absorption or metallic organic dye complexes, although it is preferred that at least some of the agglutinating agent be absorbed into the matrix such that it may be solubilized in the presence of a blood sample.

Suitable agglutinating agents include natural and synthetic water soluble polymers including, but not limited to, those discussed in the background. Among the available agglutinins, preferred agglutinins include hexadimethrine bromide, which is available from Aldrich Fine Chemicals as Polybrene ®, polylysine, and anti-red blood cell antibodies. It is believed that positively charged polyelectrolytes, such as Polybrene ® and polylysine, aggregate erythrocytes due to charge neutralization, changes in hydration, polymer bridging and osmotic interaction. IgG- or IgM-class antibodies specific for red blood cell antigens cause agglutination by binding to similar antigenic determinants on the surface of two separate erythrocytes which causes the cells to adhere to one another. An additional enhancement of the agglutination process is achieved by incorporating substances such as polyvinyl pyrrolidone (PVP) which apparently function as dielectrics, allowing charged cells to approach one another and be crosslinked by antibody and or other agglutinins.

A high agglutinating agent concentration results in a longer residence time for a blood sample within the matrix and increases the efficiency of agglutination of red blood cells within the matrix. This can have the undesirable effect, however, of trapping a large proportion of the plasma within the matrix. Conversely, lowering the agglutinating agent concentration allows more plasma to be released, but may result in fewer red blood cells within the sample being trapped by the matrix. The length, volume, and porosity of the matrix, as well as the volume of the blood sample to be filtered by the matrix, in addition to the agglutinating agent concentration affect the efficiency of entrapment of red blood cells within the matrix and the amount of plasma eluted by the matrix.

According to a first preferred embodiment of the device of the present invention, the pore size of the matrix is selected in conjunction with the length and volume of the matrix, the volume of blood sample to be treated, and the agglutinating agent's ability to cause the red blood cells to clump together, such that substantially all of the red blood cells present in a whole blood sample become agglutinated and are retained in the matrix. Removal of "substantially all" red blood cells present in a blood sample constitutes the removal of a sufficient amount of the red blood cells from the sample so that a clinical determination of a selected blood analyte may be performed without interference. Preferably, removal of "substantially all" red blood cells present in a blood sample constitutes the removal of at least about 90% of the red blood cells from the sample.

According to one method of utilizing the first preferred embodiment of the device of the present invention, a sample of whole blood is applied to an inlet or first end of the matrix. The blood rapidly passes through the interstices of the matrix, quickly coming in contact with the red blood cell agglutinating agents incorporated therein. These agents promote agglutination of the red blood cells which are then entrapped within the interstices of the matrix. This entrapment of the agglutinated red blood cells within the matrix permits the rapid and efficient separation of plasma or serum from the red blood cells. Additionally, because the matrix retains only a minimal amount of plasma or serum, a large amount of the plasma or serum may be successfully harvested from the whole blood sample. Optionally, a filter means such as filter paper or an additional porous matrix may be placed in liquid receiving relationship with the outlet of the matrix in order to wick the serum or plasma from the matrix.

Figure 2:
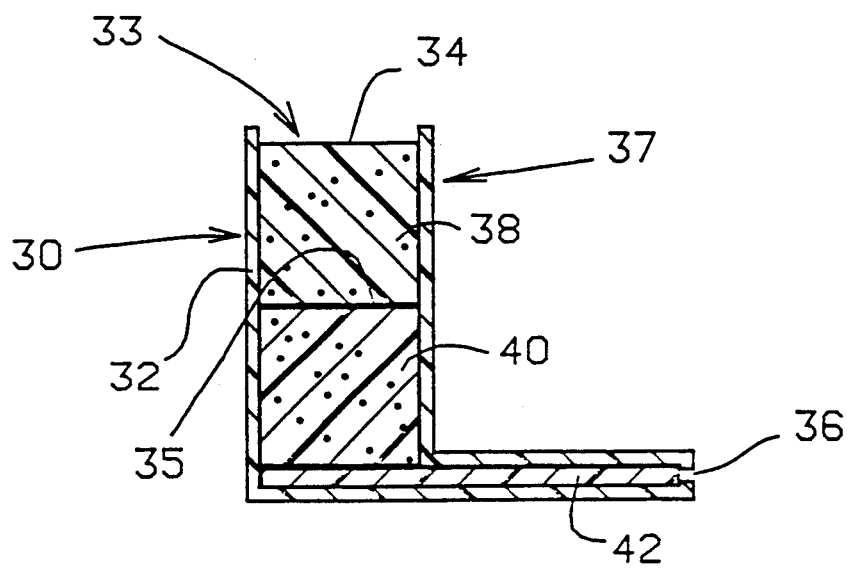
FIG. 2 is a depiction of a device comprising a first porous matrix, a second porous matrix, and a filter paper receiving matrix.

FIGS. 1-2 are depictions of exemplary devices used to separate plasma from whole blood according to the first embodiment of the present invention. As illustrated in FIG. 1, an apparatus (10) comprises a housing (12) which has an entry port (13) and an exit vent (16). Located within the housing (12) is a device (17) comprising a porous polyethylene matrix (18) which contains an agglutinating agent and is molded into a cylindrical shape having the dimensions of 3.5 mm in diameter and 5 mm in height. The exact shape and dimensions are not critical to the invention but affect resident time and efficiency as described herein. Also located within the housing (12) is a paper matrix (20). The matrix (18) has an inlet (14) and an outlet (15) and is in liquid receiving contact with said paper matrix (20). The paper matrix (20) and the matrix (18) may contain the reagents necessary for the analysis of a selected blood analyte. An embodiment of this device is described in co owned and co-pending U.S. patent application Ser. No. 335,006 filed concurrently herewith and incorporated herein by reference.

As illustrated in FIG. 2, an apparatus (30) comprises a housing (32) which has an entry port (33) and an exit vent (36). Located within the housing (32) is a device (37) comprising a first porous polyethylene matrix (38). Also located within the housing (32) is a second porous polyethylene matrix (40) in liquid receiving relationship with said first matrix and a paper matrix (42) in liquid receiving relationship with said second matrix. The first matrix (38) contains an agglutinating agent and has an inlet (34) and an outlet (35). The second matrix (40) contains some of the reagents necessary for the determination of a specific blood analyte while the paper matrix (42) contains the other components of the reagent system. It is contemplated that the first matrix (38) may also contain reagents necessary for the analysis of a selected blood analyte. An exemplary dye paper reagent system is described in U.S. Ser. No. 204,443 filed June 9, 1988 and incorporated herein by reference.

According to a second preferred embodiment of the device capable of more rapid separation of red blood cells, the pore size of the matrix is selected in conjunction with the length and volume of the matrix, the volume of blood sample to be treated, and the agglutinating agent's ability to cause the red blood cells to clump together, such that less than all the red blood cells present in a whole blood sample become agglutinated and are retained in the matrix. In these cases where it is desirable to select a matrix having a relatively large pore size which provides a high rate of flow, but wherein not all the red blood cells are retained by the matrix, the red blood cells remaining in the plasma or serum are subjected to subsequent filtration steps utilizing secondary matrices or filters alone, or impregnated with red blood cell agglutinating agents, such that "clear" plasma or serum is produced. The removal of at least 97% of the red blood cells from the sample constitutes "clear" plasma or serum.

Filter paper characterized by a pore size such that agglutinated red blood cells will not pass through it may be used to purify further the serum or plasma. Additionally, this filter paper has agglutinating agents incorporated within it to aid in the retention of the remaining red blood cells. The use of filter paper as a separate barrier for the retention of the red blood cells from the serum or plasma which flows from a matrix allows for a variety of filtration formats where a series of matrices treated with agglutinating agents are interspersed with pieces of filter material. Among the types of filters contemplated for such use are filters comprised of derivatized or underivatized cellulose, nylon, natural or synthetic membranes, or porous polyethylene matrices characterized by a pore size such that individual or agglutinated red blood cells will be retained by the porous matrix. Where more than one matrix is used, pore diameters are chosen to promote flow from one region to another.

Figure 3:
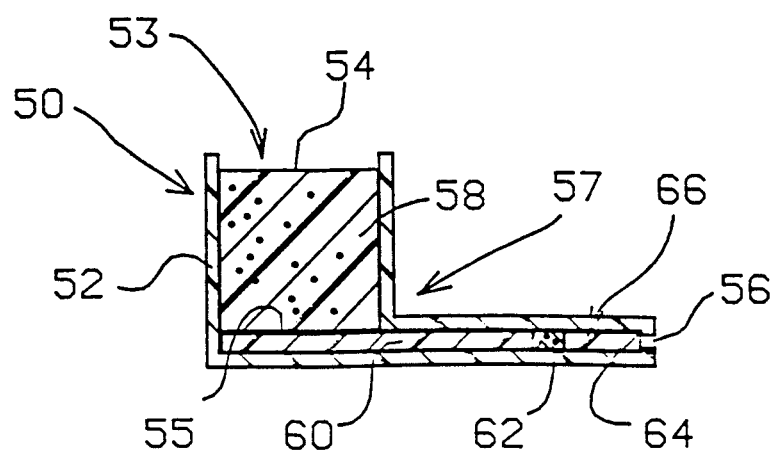
FIG. 3 is a depiction of a device comprising a porous matrix, and a filter paper receiving matrix with a reagent containing zone.
Figure 4:
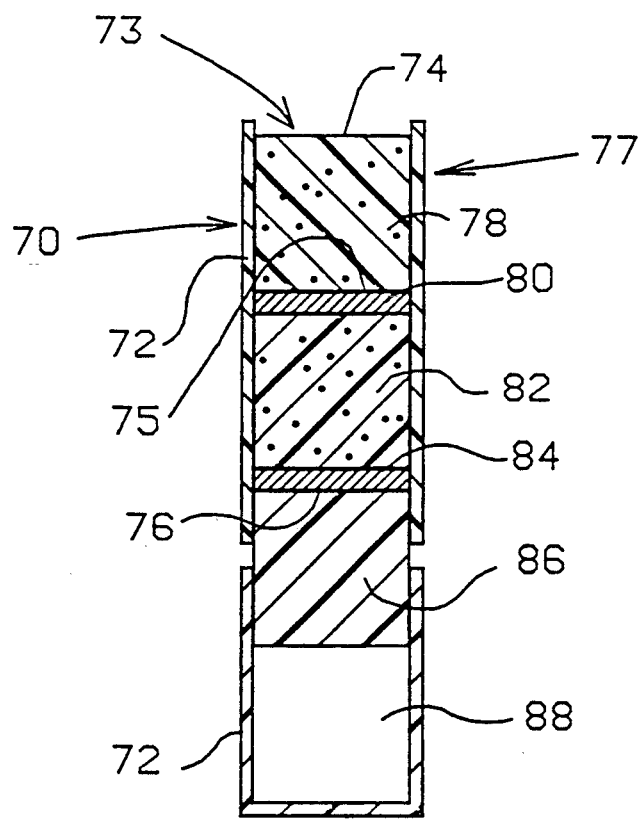
FIG. 4 is a depiction of a device comprising a first porous matrix, a first filter means, a second porous matrix, a second filter means, and a receiving porous matrix.
Figure 5:
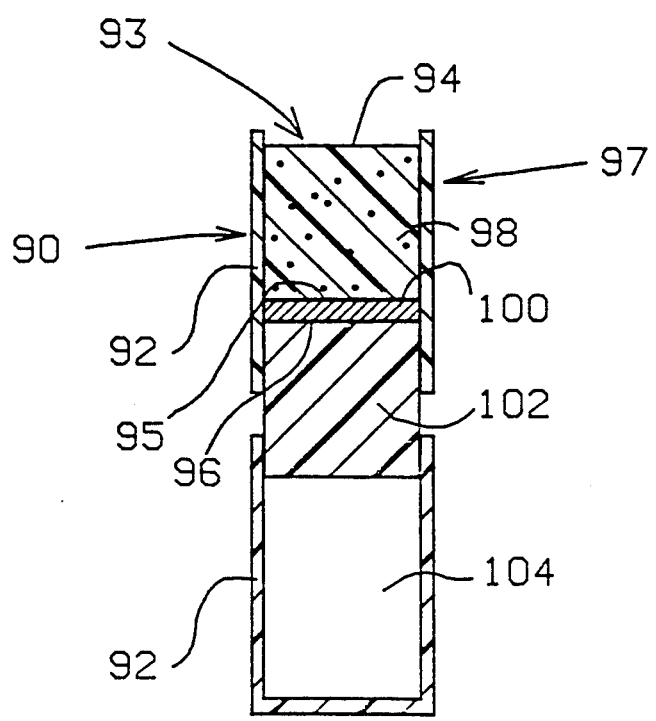
FIG. 5 is a depiction of a device comprising a porous matrix, a filter means, and a receiving porous matrix.

FIGS. 3-5 are depictions of exemplary devices used to separate plasma from whole blood according to the second embodiment of the present invention. As illustrated in FIG. 3, an apparatus (50) comprises a housing (52) which has an entry port (53) and an exit vent (56). Located within the housing (52) is a device (57) comprising a porous polyethylene matrix (58) and a paper matrix (66). The matrix (58) contains an agglutinating agent, has an inlet (54) and an outlet (55), and is in liquid receiving relationship with the paper matrix (66). The paper matrix contains a final red blood cell filtration region (60), an analyte reagent region (62), and a quantitative analysis region (64).

The present invention also provides a novel means of collecting and retaining a predetermined amount of plasma or serum for analysis in a diagnostic assay. The novel method involves a metering matrix which enables the reproducible collection of discrete amounts of plasma or serum. This process is enabled by the use of a sintered porous matrix material which is selected for the following characteristics: a reproducible fluid uptake capacity that is proportional to the fixed dimensions of the matrix, a minimal reactivity with plasma or serum components, and a hydrophilic internal surface. These characteristics enable the matrix to collect and retain a predetermined volume of sample suitable for analysis in a diagnostic assay. Preferably, the matrix material is rigid for ease of handling, and optionally, the material is chosen as having the largest void capacity for the designated matrix dimensions. With such a matrix, the collection of the sample is independent of the level of the user's training, and there is no need for sophisticated measuring equipment.

A further advantage of the present invention is that the matrices can be used as components of diagnostic devices, such as flow through and test strip devices, to collect a predetermined amount of sample that is not dependent upon the absorptive capacity of the paper, fiber and nitrocellulose materials typically used in such devices or upon the combined absorptive capacity of the device components. For example, in a test strip device the length of the strip typically determined the volume of sample which can be absorbed, and the dimensions of the test strip determine the amount of sample which will pass through the reaction and detection zones on the test strip. The matrix devices of the present invention, however, enable the collection and retention of a predetermined sample volume as well as the analysis of the entire sample volume, either within the matrix itself or within a sample receiver means to which the sample is transported, after the collection by the metering matrix of the total sample volume to be analyzed.

There are several different materials which can provide a volume measuring characteristic. These materials include paper, derivatized cellulose, porous plastic membranes and sintered porous materials. However, not all of these materials are equally suitable for use as metering matrices in diagnostic devices. For example, while a paper matrix may have the capacity to collect a sample of sufficient volume, paper matrices showed poor reproducibility in collecting that sample volume. Nylon matrices also have unacceptable reproducibility. The poor producibility of such matrices was attributed to the less sturdy and less resilient nature of such materials in withstanding handling stresses. Conversely, while matrices made from Nitrocellulose (Micron Separated, Inc., Westburough, Mass.) and Ultrabind (Gelman Sciences, Ann Arbor, Mich.) exhibit suitable reproducibility in volume metering, these materials are not suitable for the manufacturing of matrices of sufficient thickness to collect and retain a quantity of sample typically needed for analysis. Porous sintered materials, however, possess the structural rigidity and the void capacity to meet these needs.

Other features of the selected material which are important to collection or metering matrix performance include the particle size and pore size of the sintered material used to form the matrix. For example, a suitable metering matrix pore size was found to relate to the configuration of the device in which the matrix might be used. In a configuration where the metering matrix is situated directly below and in contact with the blood separator means, the flow dynamics through the matrix are less of a concern. If the matrix is situated laterally to the blood separator means, and a transfer material such as a wicking layer or strip is used to transport the plasma from the separator means to the matrix, then the pore size of the matrix should be large enough to induce sample collection by the matrix while maintaining even sample distribution within the matrix. The pore size of the matrix, however, cannot be too large in comparison to that of the strip. A large difference in capillary diameter becomes a dominant factor in flow resistance; the sample may wick along the fine pore channels but courser channels could be bypassed. When the wicking strip material is cellulose or a cellulose derivative, a metering matrix pore size in the range of about 5 um to about 100 um is typically used. Preferably, a pore size in the range of about 10 um to about 25 um is used. A most preferred pore size is about 15 um, estimated by a mercury intrusion method, which is graded as "fine" pore. Pore sizes in the range of about 5 um to about 1 um are usable as super fine pore sizes in metering matrix materials. In addition, if such a lateral configuration is used with a wicking strip to transport the sample from the blood separator means to the collection or metering matrix, the filling of the matrix can be maximized by directing the sample flow to the matrix. The term "directing the flow" refers to the placement of the matrix at the end of the wicking strip or over a slit or space in the strip such that the entire adjacent surface of the matrix does not directly contact the strip material, i.e., a substantial portion of the matrix surface is not in physical contact with the strip. By using this directed flow format, the sample is deterred from bypassing the matrix and continuing through the strip material.

In an alternative embodiment of the present invention, the metering matrix material can be modified to alter its manufactured pore size. For example, a porous matrix of sintered polyethylene which has been manufactured to have a certain nominal pore size can be coated with a treatment material, such as dextran, polyethylene glycol or carboxylatex, to produce a matrix which has sample collection and flow attributes characteristic of finer pored matrices. By treating the matrix, the void capacity of the matrix can be decreased and the flow rate through the matrix can be changed to simulate the characteristics of a matrix having a smaller pore size.

Another desired attribute of the collection matrices of the present invention is the hydrophilic nature of the matrices. However, because sintered materials are generally not hydrophilic, matrices made of sintered material are rendered hydrophilic by treatment with surfactants, as described above in the treatment of the blood separator means. Surfactant solution concentrations of about 0.1% to about 0.5% are used to treat matrices of sintered polyethylene and thereby improve the performance of the matrices. With excess surfactant, the addition of sample can dissolve the surfactant and generate foam which could block the pores and capillaries of the matrix. With not enough surfactant or an uneven distribution of surfactant, there can be hydrophobic pockets within the matrix through which plasma does not readily flow.

In another embodiment of the present invention, the plasma or serum sample collected and retained by the matrix can be eluted from the matrix by the addition of a buffer. The eluted sample and buffer can be gathered by any suitable receiving means. For example, the sample can be eluted into a test tube, cuvette or reaction well or onto a slide. Optionally the receiving means can contain all or some of the reagents necessary to perform the diagnostic assay of the sample. Alternatively, the matrix can be contacted to a receiving means such as an absorbent material will have a pore size smaller than that of the matrix, to induce the transport of sample from the matrix. Any suitable absorbent material can be used, such as a chromatographic, bibulous, porous or capillary material or other conventional absorbent material well-known to those skilled in the art, and the material can optionally contain all or some of the reagents necessary to perform the diagnostic assay. The sample receiver means of a diagnostic device can be in direct contact with the collection matrix throughout use or it may be brought into contact with the matrix after the matrix has collected the predetermined volume of test sample.

Generally, the metering matrix is enclosed or housed within a nonabsorptive casing material such that a matrix inlet port and, optionally, an exit port are defined. Such devices are illustrated in FIGS. 4 and 5. FIGS. 4 and 5 also illustrate the use of the collection matrix in conjunction with the blood separator means. In a vertical device configuration as shown in FIGS. 4 and 5, the housing material is chosen to minimize the effects of gravity upon the transport of sample from the blood separator means to the collection or metering matrix. The effects of gravity were minimized in the present invention by molding the housing from a material which has minimal interaction with plasma or serum. Suitable housing materials include polystyrene, acrylic, polycarbonate, teflon, polypropylene, polyethylene and silicon. A particularly preferred housing material is KR003 resin, a styrene-butadiene copolymer (Phillips 66, Bartlefville, Tex.), due to its minimal interaction with plasma. Such a housing also prevents the overfill of the collection matrix by minimizing the plasma contact between the collection matrix and the housing. With the use of a housing, a matrix of given dimensions and nominal pore size will provide a reproducible void capacity and reproducible flow results, as demonstrated in the examples which follow.

As illustrated in FIG. 4, an apparatus (70) comprises a housing (72) which has an entry port (73) and an exit port (76). Located within the housing (72) is a device (77) comprising a first porous polyethylene matrix (78), a first filter means (80), a second porous polyethylene matrix (82), and a second filter means (84). The first matrix (78) contains an agglutinating agent and has an inlet (74) and an outlet (75). Because the first filter means (80) is sandwiched between the first matrix (78) and the second matrix (82), the top of the first filter means (80) is in liquid receiving relationship with the outlet (75) of the first matrix (78), and the bottom of the first filter means (80) is in liquid receiving relationship with the top of the second matrix (82). The bottom of the second porous polyethylene matrix (82) is then in liquid receiving relationship with the top of the second filter means (84). Prior to addition of a blood sample to the device, it is placed on top of and in liquid receiving relationship with a third porous polyethylene matrix (86). This third matrix (86) is designed to retain and receive within its void space a selected predetermined volume of plasma which is then washed into a receiving cuvette (88). The third matrix (86) may contain some of the reagents necessary for the determination of a specific blood analyte while the cuvette (88) may contain other components of the reagent system.

As illustrated in FIG. 5, the device (90) comprises a housing (92) which has an entry port (93) and an exit port (96). Located within the housing (92) is a device (97) comprising a porous polyethylene matrix (98) and a filter means (100). The matrix (98) contains an agglutinating agent and has an inlet (94) and an outlet (95). The top of the filter means (100) is in liquid receiving relationship with the outlet (95) of the matrix (98). Prior to addition of a blood sample to the device (90), it is placed on top of and in liquid receiving relationship with a second porous polyethylene matrix (102). This second matrix (102) is designed to receive and retain a selected predetermined volume of plasma which is then washed into a receiving cuvette (104). The second matrix (102) may contain some of the reagents necessary for the determination of a specific blood analyte while the cuvette (104) may contain other components of the reagent system.

The plasma or serum which flows from the devices of the present invention may flow directly into a receiving matrix. Among the different types of matrices available which may receive the plasma or serum from the device are a dye paper matrix (see, e.g. U.S. Ser. No. 204,443 above) to which the analytical reagents have been attached or porous matrices made from sintered materials, such as glass, steel, ceramics, or plastic polymers, which are capable of retaining a selected volume of plasma or serum. According to use of the dye paper matrix, the plasma or serum enters the paper and flows as a front through the paper. It comes in contact with the analytical reagents incorporated in the paper and the assay for the desired blood component is performed on the paper.

The preferred sintered matrix capable of receiving the flow of plasma or serum from the device is a treated porous polyethylene matrix. The plasma or serum flows from the device and a selected amount enters the receiving matrix. The void space of the receiving matrix determines the volume of plasma or serum which may enter the receiving matrix. The plasma or serum is eluted from the receiving matrix into a cuvette by addition of an elution buffer. Analysis of the desired blood component occurs within the cuvette which may contain the desired analytical reagents. The porous polyethylene matrix may also contain reagents necessary for the analysis of the analyte after plasma or serum have been eluted. Such an analysis may take place in the polyethylene matrix or the sample and reagents may be eluted into the cuvette for subsequent reading.

Although the devices of the present invention may be used generally as a means for providing plasma or serum for use in other diagnostic procedures, various analytical reagents may be incorporated into the devices in order to render them suitable for carrying out an analysis for a selected component of blood plasma or serum. Among those contemplated are the reagents such as those utilized for carrying out enzymatic analysis of analytes such as cholesterol, triglycerides, and glucose in the blood. It is contemplated that reagents for a wide variety of assays may be incorporated into the devices of the present invention.

The porous matrices of the invention will retain serum or plasma in their interstices in proportion to the volume of the porous matrix. Red blood cell free plasma or serum will generally remain in the interstices of the porous matrix unless it is removed by external means. Such external means can include the use of positive hydrostatic pressure such as may be obtained by application of additional blood sample or elution buffer to the matrix. Alternatively, filter means such as filter paper or additional porous matrices in liquid receiving relationship with the matrix may be used to induce the flow of plasma or serum by capillary action out of the matrix. Accordingly, it is desired to use the smallest matrix consistent with flow and purity considerations in order to maximize serum or plasma yield.

The rate of flow of plasma and serum through the porous matrix may be controlled by varying the porosity and flow properties of the contacting filter means. It is contemplated that filter means may be selected to induce rapid flow through the porous matrix. Alternatively, where it is desired to maintain a longer residence time of blood sample within the porous matrix, a filter means providing a relatively slower rate of fluid flow out of the porous matrix may be selected. It is contemplated that slowing the rate of flow through the porous matrix can increase the efficiency of agglutination within the matrix. It is further contemplated that use of a filter means inducing a relatively slow rate of fluid flow can provide the advantage of greater agglutination efficiency and may also allow use of a smaller porous matrix thus providing the additional advantage of maximizing plasma or serum yield.

The following specific examples are directed to several embodiments of the present invention and are not to be construed as limiting the scope of the invention.

EXAMPLE 1

The device depicted in FIG. 2 contains a first matrix which has dimensions of 5 mm×4 mm×3 mm, is treated with a wetting agent and has adsorbed to it a 30 microliter solution of 5 mg/ml anti-red blood cell antibodies in 100 mM citrate, pH 5.6. The pore size of the first matrix and the agglutinating agents adsorbed to it are selected to retain substantially all red blood cells within the matrix. Loading is accomplished by saturating the first matrix with the antibody solution. Once the matrix is loaded, it is frozen and lyophilized. The second matrix, which has dimensions of 6 mm×4 mm×0.8 mm, is treated with a wetting agent and contains the reagents necessary for determination of an analyte in the plasma. Whole blood is added through the entry port and, as it percolates through the first matrix, red blood cells within the sample are agglutinated by the anti red blood cell antibodies and the clumps are filtered out. The plasma, now free of red blood cells, flows from the first matrix into the second matrix and solubilizes the enzymes and dye component of the reagent system located there. This mixture then flows into the dye paper matrix, where determination of the analyte occurs by reaction of the blood analyte with other enzymes and dye components of the reagent system.

EXAMPLE 2

The device depicted in FIG. 3, which has dimensions of 6 mm×4 mm×0.8 mm, is treated with a wetting agent and has adsorbed to it 8 microliters of a 5 mg/ml solution of anti red-blood cell antibodies: IgG fraction (Organon Teknika Corp., Cappel Division), in 100 mM citrate buffer, pH 5.6. Loading is accomplished by applying the antibody solution to the matrix under vacuum. Once the matrix is loaded, it is frozen and lyophilized. Whole blood is added through the entry port and, as it percolates through the matrix, red blood cells within the sample are agglutinated by the anti-red blood cell antibodies and the red blood cells are partially filtered out. Final red blood cell filtration occurs in the filtration region of the dye paper matrix. As the plasma continues flowing up the dye paper matrix, it contacts the analyte reagent region where the reagents for analyte determination have been lyophilized. The plasma solubilizes these reagents and quantitation of the analyte by reaction of the sample and reagents occurs in the quantitative analysis region.

EXAMPLE 3

In this example, the device disclosed in Example 2 was used to separate plasma from whole blood so that a blood cholesterol assay could be performed. The matrix was loaded with a solution of 8 microliters of 5 mgml anti-red blood cell antibodies: (IgG fraction (Organon Teknika Corp., Cappel Division)), 10 mgml cholesterol esterase, 10 mgml horseradish peroxidase, and 5 mg/ml 4-aminoantipyrine in 100 mM citrate, at pH 5.6. The device was placed on top of and in contact with a dye paper matrix and whole blood was added to the device through the entry port. As the blood percolated through the porous matrix, red blood cells within it were agglutinated by the anti-red blood cell antibodies and the red blood cells were partially filtered out by the matrix. Final red blood cell filtration occurred in the region of the dye paper matrix which was 5–6 mm from the paper origin where the device contacted the dye paper matrix. At this point 5–6 mm from the paper origin, the plasma contacted an analyte determinator region which was a 3 mm wide zone that contained a solution of 100 mg ml cholesterol oxidase, 1% (w/v) triton X-100, and 100 mM NaPO4, at pH 6.8. As the plasma flowed up the paper matrix it solubilized the lyophilized reagents. The flow continued into the dye paper matrix where quantitation of the analyte (cholesterol) occurred.

EXAMPLE 4

With respect to the device depicted in FIG. 1, the matrix was treated with a wetting agent and had adsorbed to it various 25 microliter solutions of anti red blood cell antibodies: IgG fraction (Organon Teknika Corporation, Cappel Division), in 20 mM citrate buffer, pH 5.6. In this device, the data listed in Table 1 below indicated that a 2 mg/ml antibody concentration loaded under vacuum was optimal for filtering out red blood cells from whole blood having a hematocrit of 30–60% red blood cells and releasing at least 5 microliters of plasma from a 25 microliter sample of whole blood. Hematocrit refers to the percentage of the volume of a blood sample occupied by red blood cells. For example, a 25 microliter blood sample with a hematocrit of 30 contains 7.5 microliters of red blood cells and 17.5 microliters of plasma. The whole blood samples were treated with heparin as an anticoagulant. This concentration of antibody allowed plasma to flow 12 mm to the end of the filter paper in a reasonable amount of time, while still retaining substantially all the red blood cells of a sample within the matrix. Higher antibody concentrations resulted in greater agglutination which blocked the pores within the matrix and precluded flow of plasma. The pore size of the matrix and the agglutinating agents adsorbed to it were selected to retain substantially all red blood cells within the matrix. Loading was accomplished by applying the antibody solution to the matrix by saturation, i.e. soaking the matrix in solution, or under vacuum, i.e. soaking the matrix in solution and pulling a vacuum on it for 10 minutes. It was determined that loading under vacuum was superior to loading by saturation because vacuum loading ensures that no air pockets remain in the matrix after loading. Loading by saturation does not ensure this same result. Once the matrix was loaded, it was frozen and lyophilized. The trials were run in sets of 6 and a trial was determined to be "substantially free" of red blood cells (i.e. "No RBCs") by the visual determination that there were no red blood cells in the filter paper, which was in liquid receiving relationship with the matrix, after the filtration step. In the table, "seconds to end" refers to the elapsed time from the addition of a blood sample to the inlet of the matrix, until plasma reached the end of the filter means.

TABLE 1

| | ANTI-RED BLOOD CELL ANTIBODIES (mg/ml) | | | | |
|---|---|---|---|---|---|
| | 1 | 2 | 3 | 4 | 5 |
| HEMATOCRIT = 30 | | | | | |
| Saturated | | | | | |
| seconds to end | 74.5 | 82.0 | 104.2 | 159.7 | 219.3 |
| no RBCs | 2/6 | 5/6 | 6/6 | 6/6 | 5/5 |
| Vacuum | | | | | |
| seconds to end | 65.3 | 70.2 | 105.2 | 84.2 | 108.8 |
| no RBCs | 2/6 | 4/6 | 6/6 | 6/6 | 6/6 |
| HEMATOCRIT = 45 | | | | | |
| Saturated | | | | | |
| seconds to end | 200.0 | 290.0 | 585.6 | 631.7 | 469.8 |
| no RBCs | 5/6 | 6/6 | 5/5 | 5/5 | 5/5 |
| HEMATOCRIT = 45 | | | | | |
| Vacuum | | | | | |
| seconds to end | 107.0 | 326.7 | 193.0 | 414.8 | n.f. |
| no RBCs | 6/6 | 4/4 | 5/5 | 6/6 | n.f. |
| HEMATOCRIT = 60 | | | | | |
| Saturated | | | | | |
| seconds to end | 336.7 | 700.7 | n.f. | n.f. | n.f. |
| no RBCs | 2/3 | 3/3 | n.f. | n.f. | n.f. |
| Vacuum | | | | | |
| seconds to end | 354.3 | 824.5 | n.f. | n.f. | n.f. |

TABLE 1-continued

| | ANTI-RED BLOOD CELL ANTIBODIES (mg/ml) | | | | |
|---|---|---|---|---|---|
| | 1 | 2 | 3 | 4 | 5 |
| no RBCs | 5/5 | 4/4 | n.f. | n.f. | n.f. | n.f. = no flow of plasma to end of filter paper matrix.

At a low blood hematocrit (e.g. 30), up to 15 microliters of plasma may be released from a 25 microliter sample of whole blood in as little as 2 minutes, while at a high blood hematocrit (e.g. 60), about 5 microliters of plasma may be released from a 25 microliter sample of whole blood in around 15 minutes.

EXAMPLE 5

In this example, the device disclosed in Example 3 was used to separate plasma from whole blood so that an assay to detect antibodies to Human Immunodeficiency Virus (HIV) could be performed. The matrix was loaded with 8 microliters of 5 mg/ml anti-red blood cell antibodies: (IgG fraction (Organon Teknika Corp. Cappel Division)), 5 microliters detector label prepared by binding 10 micrograms/ml HIV antigen with 0.05% black latex as described in co-owned and co pending U.S. patent application Ser. No. 248,858 filed Sept. 23, 1988, poly(pyrrole), in aqueous suspension at pH 7.0. The device was placed on top of and in contact with a 3×30 mm strip of nitrocellulose (S & S, Keene, N.H.), which had a 5 micrometer pore size, and 30 microliters of whole blood were added to the device through the entry port. As the blood percolated through the porous matrix, red blood cells within it were agglutinated by the anti-red blood cell antibodies and the red blood cells were partially filtered out by the matrix. The plasma in the sample mixed with the label suspension in the matrix and then entered the nitrocellulose strip where final red blood cell filtration and analysis of the separated plasma occurred.

EXAMPLE 6

To the device depicted in FIG. 4, whole blood is added through the entry port. As the blood percolates through the first matrix, red blood cells within the sample are agglutinated by the anti-red blood cell antibodies and the red blood cells are partially filtered out. The remaining red blood cells and smaller clumps of agglutinated red blood cells pass into the first filter where additional separation of plasma from the red blood cells occurs. Those red blood cells not retained by the first filter pass into the second matrix where additional separation of plasma from the red blood cells occurs. Finally, any red blood cells not retained by the second matrix pass into the second filter, to which at least one red blood cell agglutinating agent has been adsorbed, where agglutination of the remaining red blood cells in the plasma occurs. The plasma then flows into the receiving matrix where the plasma volume is quantitated. The red blood cell filtration stack is separated from the receiving matrix and the selected volume of plasma is eluted into an attached cuvette by the addition of the elution buffer. The cuvette may contain various analytical reagents. Thorough mixing of the plasma and the elution buffer is accomplished by inverting the cuvette 2 times. After a specified waiting period, the results of the test are obtained by comparing the color of the liquid with a standard chart.

Specifically, with respect to the device depicted in FIG. 4, the pore size of the first matrix (Porex 4897) and the agglutinating agents adsorbed to it were selected to agglutinate and retain most, but not all, red blood cells within the first matrix. The first matrix is molded into a cylindrical shape having the dimensions of 0.2 inches in diameter and 0.07 inches in length and had adsorbed to it 15.0 microliters of a solution of 0.44% (w/v) antiserum to red blood cells (Organon Teknika Corp., Cappel Division), 4.4% (w/v) Polybrene (Aldrich Fine Chemicals), and 4.4% (w/v) PVP (Aldrich Fine Chemicals) in 0.35 mM citrate buffer, pH 7.4 (Fisher Chemicals). The coated first matrix was dried in a hot air oven. The composition of the solution and the quantity loaded into the first matrix were chosen to provide very rapid red blood cell agglutination without causing red blood cells to lyse and without causing hemodilution. The remaining red blood cells were removed from the plasma by passing it through the first filter means (Whatman 31 ET), the second porous polyethylene matrix (Porex 4932), and the second filter means (Whatman 31 ET). This last filter means had incorporated within it 36.1 microliters/cm$^2$ of a 1 mg/ml solution of antiserum to red blood cells. The coated last filter means was dried in a hot air oven. This device produced 15 microliters of clear plasma 99% free of hemoglobin from 50 microliters of blood within 3 minutes as shown in Table 2. Upon removal of the red blood cell filtration stack, i.e. the first matrix, the first filter means, the second matrix, and the second filter means, the plasma was eluted into a cuvette by the addition of an elution buffer.

EXAMPLE 7

To the device depicted in FIG. 5, whole blood is added through the entry port. As the blood percolates through the matrix, red blood cells within the sample are agglutinated by the anti red blood cell antibodies and the red blood cells are partially filtered out. The remaining red blood cells and smaller clumps of agglutinated red blood cells pass into the filter where additional separation of plasma from the red blood cells occurs. The plasma then flows into the receiving matrix where the plasma volume is quantitated. The red blood cell filtration stack is separated from the receiving matrix and the selected volume of plasma is eluted into an attached cuvette by the addition of the elution buffer. The cuvette may contain various analytical reagents. Thorough mixing of the plasma and the elution buffer is accomplished by inverting the cuvette 2 times. After a specified waiting period, the results of the test are obtained by comparing the color of the liquid with a standard chart.

Specifically, with respect to the device depicted in FIG. 5, the pore size of the matrix (Porex 4897) and the agglutinating agents adsorbed to it were selected to agglutinate and retain most, but not all, red blood cells within the matrix. The matrix had adsorbed to it 15.0 microliters of a solution of 0.88% (w/v) antiserum to red blood cells (Organon Teknika Corp., Cappel Division), 1.76% (w/v) Polybrene (Aldrich Fine Chemicals), and 1.76% (w/v) PVP (Aldrich Fine Chemicals) in 0.397 mM citrate buffer, pH 7.4 (Fisher Chemicals). The coated matrix was dried in a hot air oven. The composition of the solution and the quantity loaded into the matrix were chosen to provide very rapid red blood cell agglutination without causing red blood cells to lyse and without causing hemodilution. The remaining red blood cells were removed from the plasma by passing it through the filter means (Whatman 1CHR). The filter means had incorporated within it 15.0 microliters/cm² of a 1 mg/ml solution of antiserum to red blood cells. The coated filter means was dried in a hot air oven. This device produced 10 microliters of clear plasma 99% free of hemoglobin from 40 microliters of blood within 2 minutes as shown in Table 3. Upon removal of the red blood cell filtration stack, i.e. the matrix and the filter means, the plasma was eluted into a cuvette by the addition of an elution buffer.

weighed, and the matrix was soaked in the sample. The matrix was then removed from the sample, and the excess sample was removed from the matrix surface by quick-blotting with a coarse-pore material such as cellulose (Kim Wipe, Kimberly Clark, Ga.). The difference in weight between the wetted and the dry matrix material indicated the void capacity of the matrix. Table 4 illustrates the results of the void capacity determinations for several different matrix materials, including

TABLE 2

BLOOD SEPARATOR PERFORMANCE OF FOUR LAYER STACK
(POREX-31ET-POREX-31ET. POREX)

| Receiving Frit Dimension | | Blood Sample | Hematocrit of | Time | | | Plasma Volume |
|---|---|---|---|---|---|---|---|
| Diameter (mm) | Thickness (mm) | Volume (uL) | Sample (%) | Plasma Appeared in Frit (Seconds) | Frit Appeared Full (Seconds) | Device Separated (Seconds) | Quantitate (uL) |
| 3.5 | 3.4 | 50 | 25 | 10 | 60 | 120 | 15.5 |
|  |  | 50 | 38 | 15 | 90 | 120 | 15.3 |
|  |  | 50 | 50 | 20 | 120 | 180 | 15.1 |
|  |  | 50 | 75 | 60 | NO | 900 | about 5 |
|  |  | 75 | 75 | 50 | NO | 600 | about 10 |

TABLE 3

BLOOD SEPARATOR PERFORMANCE OF TWO LAYER STACK
(POREX-1chr.POREX)

| Receiving Frit Dimension | | Blood Sample | Hematocrit of | Time | | | Plasma Volume |
|---|---|---|---|---|---|---|---|
| Diameter (mm) | Thickness (mm) | Volume (uL) | Sample (%) | Plasma Appeared in Frit (Seconds) | Frit Appeared Full (Seconds) | Device Separated (Seconds) | Quantitate (uL) |
| 3.5 | 1.7 | 35 | 35 | 10 | 30 | 120 | 8.7 |
|  |  | 35 | 40 | 10 | 30 | 120 | 8.6 |
|  |  | 35 | 45 | 10 | 40 | 120 | 8.5 |
|  |  | 35 | 50 | 15 | 40 | 120 | 8.4 |
|  |  | 40 | 55 | 15 | 50 | 120 | 8.3 |
|  |  | 50 | 60 | 20 | 60 | 120 | 8.2 |

EXAMPLE 8

Several methods can be used to estimate the void volume and the metering capacity of the collection matrices. When the materials are thin and have different appearances when dry or wet, a diffusion wicking method was used. In this method, a fixed volume of sample was applied to the surface of the matrix by precision pipetting. The diameter of the wet spot on the matrix surface, following the diffusion process, provided information about the volume capacity and reproducible sample collection of the matrix material.

Chromatography paper matrices (31ET cellulose paper, Whatman Applied Technology Business, Kent, England) had about the same volume capacity as nitrocellulose matrices (5.0 μm pore, Micron Separated, Inc.), but the reproducibility of sample collection was better with the paper matrices (2% variation) as compared to the nitrocellulose (3.4% variation). Ultrabind membrane matrices (Gelman) demonstrated good reproducibility (2% variation), but these matrices had a low volume capacity due to the thinness of the material. While it is possible to coat nitrocellulose to form a thicker matrix material, such matrices were extremely fragile.

When the material of interest was not translucent, and when a determination of the total saturation capacity of the material was desired, a method of weighing the matrix before and after sample collection was used. The matrix was cut to a uniform dimension (discs having a surface area of 1.13 square centimeters) and sintered polyethylene (Porex 4897, Porex Technologies, Inc, Fairburn, Ga.) and nylon (nylon mesh, Spectrum Medical Industries, Inc., Los Angeles, Calif.).

TABLE 4

| Void Capacity by Wet-Blot-Weighing Method | | | | |
|---|---|---|---|---|
| Material | Thickness (mm) | Dry Weight (mg) | Void Capacity (mg) | Void Variation (%) |
| Nitrocellulose | 0.17 | 3.8 | 17.1 | 3.5 |
| Nylon | 0.05 | 4.0 | 3.2 | 29.0 |
| Porex 4897 | 1.4 | 72.9 | 64.3 | 1.0 |
| Ultrabind | 0.17 | 7.5 | 5.9 | 3.5 |
| Whatman Paper | 0.4 | 20.5 | 40.5 | 3.9 |

A comparison of the results presented in Table 4 illustrates that the sintered polyethylene matrix material had the largest void capacity for matrix size as well as the least variation in measurements. The nylon matrix had unacceptable reproducibility. The nitrocellulose and Ultrabind matrices had an insufficient capacity for large sample volumes. While multiple layers of the latter materials could be stacked to bring the void capacity into the desired range, the reproducibility of volume metering with such stacks was less well controlled.

EXAMPLE 9

This experiment demonstrated a method for the modification of the pore size of a matrix. The modification was performed by treating the matrices with a solution of dextran (2.5% in water). The effect of coating the internal surface area of the matrix with dextran was determined by applying plasma samples having different hematocrit values to the matrices. The results of the experiment are presented in Table 5. The data show the effects of pore size and dextran coating on plasma recovery using vertical configuration devices, as shown in FIGS. 4 and 5, using similar housings. The entries are expressed as a percent of the plasma obtained from a 45% hematocrit blood specimen.

TABLE 5

Effects of Pore Size and Matrix Coating

| Blood sample Hematocrit (%) | Uncoated Large Pore Receiver (25 μm) | Coated Large Pore Receiver (25 μm) | Uncoated Small Pore Receiver (10 μm) |
|---|---|---|---|
| 0 | 150 | 132 | 110 |
| 30 | 112 | 118 | 105 |
| 45 | 100 | 100 | 100 |
| 50 | NT | 95 | 98 |
| 55 | 87 | 89.1 | 95 |
| 60 | NT | 80.4 | 90 |
| Volume (μL) at 45% hematocrit | 9 | 6.8 | 4.5 |

NT — not tested

EXAMPLE 10

Experiments were performed using different materials to manufacture the housing for the collection matrix. The most suitable housing materials were those that minimized the interaction of the housing with the plasma or serum sample. The collection matrix had the tendency to over-fill when the blood samples had a low hematocrit, because there was minimal flow resistance in the material. The collection matrix had a tendency to under-fill when the blood samples had a high hematocrit, due to the increased amount of materials in the sample which could block the pores of the collection matrix. Table 6 presents data comparing the plasma volume received and the percent recovered from collection matrices in housings made of different materials. Plasma specimens were used as test samples, and the void capacity of the sintered polyethylene collection matrix was 8.5 μL, as estimated by the wet-blot-weigh method. The expected 8.5 μL was obtained by measuring the plasma weight using blood specimens of 45% hematocrit. The housings were made from a styrene-butadiene copolymer (KR003, Phillips 66), a styrene-acrylic alloy (Q886, Monsanto, Mo.), an acrylo-butyl styrene (ABS, Monsanto, Mo.), polymethylpentene (TPX, Mitsui Petrochemical, New York, N.Y.), polypropylene (PD213, Himont, Bloomington, De.) or polyethylene (PE, GE Plastics, Pittsfield, Mass.).

TABLE 6

Housing to Minimize Matrix Over-fill

| Plastic Resin | Plasma Volume Received (μL) | % Recovery over the expected 8.5 μL |
|---|---|---|
| KR003 | 9.8 | 115 |
| Q886 | 10.6 | 124 |
| ABS | 11.0 | 129 |
| TPX | 11.6 | 136 |
| PD-213 | 10.9 | 129 |
| PE | 11.6 | 136 |

Table 7 presents plasma recovery data using collection matrices in housings made of different materials and whole blood samples of 32% hematocrit. The percent recovery was calculated from the plasma recovered from whole blood samples of 32% hematocrit in comparison to that recovered using 43% hematocrit blood as a specimen, assuming 43% hematocrit to be "100% volume".

TABLE 7

Effect of Housing on Plasma Recovery

| Housing Material | % Plasma Recovered |
|---|---|
| KR003 | 109 |
| TPX | 111 |
| PD-213 | 120 |
| PE | 114 |

The housings made of KR003 resin demonstrated the least plasma recovery variations with samples of varied hematocrit.

It is also possible to minimize the over-filling effect and hematocrit effect on plasma recovery by coating the molded plastic housings with detergent to form a hydrophobic surface or by a siliconization process using curable silicon (MDX4-4159, Dow-Corning, Midland, Mich.).

EXAMPLE 11

This experiment compared the effects of directed flow and undirected flow in diagnostic device configurations. The blood separation means was a sintered polyethylene cylinder having the dimensions of 0.074 inch in length and 0.194 inch in diameter. The pore size of the blood separator, and the agglutinating agents absorbed within the separator, were selected to rapidly agglutinate and retain within the matrix most of the red blood cells from the whole blood sample without causing hemodilution and without causing the cells to lyse. The separator had been saturated with a solution of 8.89 optical density (280 nm) mL antiserum to red blood cells (Organon Teknica Corporation, Durham, N.C.) in citrate buffer (0.397 mM, pH 7.4, Fisher Chemicals, Fairhaven, Pa.) and surfactant (0.1% Triton X-405, Sigma, St. Louis, Mo.). The separator means was then dried in a hot air oven.

The metering or plasma collection matrix was also a sintered polyethylene cylinder, having the dimensions of 0.070 inch in length and 0.150 inch in diameter. The cylinders were made by means of a hollow core punch to remove matrices of uniform size from a stock sheet of sintered polyethylene having a five micron nominal pore size (General Polymeric). The plasma collection matrix had been made hydrophilic by pretreating the sheet with a three percent suspension of carboxylatex (Seradyne, Indianapolis, Ind.) in methanol, followed by overnight drying under vacuum.

The wicking strip was composed of cellulose paper (Schleicher & Schuell #410, Keene, N.H.)

A comparison of devices was performed using an undirected flow device configuration in which the entire bottom surface of the metering matrix was in contact with the upper surface of the wicking layer, and a directed flow device configuration in which a substantial portion of the bottom surface of the metering matrix was positioned over a slit or space in the upper surface of the wicking layer or strip. Blood samples were applied to the blood separator means of the devices, wherein the red blood cells were removed and the resultant plasma entered the wicking layer by capillary force. The plasma continued through the wicking strip to the collection matrix and beyond to an overflow portion of the wicking strip. When no further movement of plasma through the overflow zone was visually observed, the collection matrix was removed and weighed. By comparing the weights of the used matrices to the known starting weights of the matrices, a net increase in weight due to plasma collection was calculated. The results are present in Table 8. The results indicate that when the lateral flow device configuration was used, the directed flow configuration provided a more uniform filling of the collection matrix over a broad hematocrit range. Under-filling of the matrix was observed with the undirected flow configuration at a 55% hematocrit.

TABLE 8

Net Increase in Weight of Matrix Due to Plasma Collection

| Configuration | Blood Hematocrit (%) | | |
|---|---|---|---|
| | 0 | 30 | 55 |
| Undirected | 4.5 mg | 5.0 mg | 1.9 mg |
| Directed | 5.0 mg | 4.7 mg | 4.0 mg |

EXAMPLE 12

The following experiment demonstrated the precision of the collection matrix and blood separator, the correlation of assay results with a reference assay and the effect of hematocrit on the performance of the assay device. A vertical blood separation stack, as illustrated in FIGS. 4 and 5 was used.

The blood separator material was prepared from sintered polyethylene (Porex 4897). The material was saturated with a solution of antiserum to human red blood cells (8.89 optical density [280 nm]/mL; Cappel 0101-1322, Organon Teknica Corporation) in citrate buffer (0.573 mM, pH 7.4, Fisher Chemicals) and surfactant (0.1% Triton X-405). The material was then dried at low, laminar air flow at room temperature.

The collection matrix material was sintered polyethylene sheet stock (General Polymerics) having a pore size of about 5 μm. The sheet was saturated with a 3% suspension of carboxylatex (Seradyne) in methanol. The solvent was then removed by holding the sheets under vacuum overnight in a desiccator.

Two discs, each 0.200 inch in diameter and 0.064 inch in length, were punched from the blood separator material and inserted into a cylindrical housing as shown in FIGS. 4 and 5. A disc of chromatography paper (0.200 inch in diameter, Whatman 1CHR) that had been coated in IgG to human red blood cells (Organon Teknica, Cappel 0201-1322) in sodium citrate buffer (2.0 mM, pH 7.4) was then placed in the housing. A disc of collection matrix material (0.138 inch in diameter, 0.064 inch in length) was punched from the matrix material. The disc dimension was chosen to provide a collection matrix with a void capacity of about five microliters. The collection matrix was inserted in the housing such that the bottom surface of the paper disc was in contact with the upper surface of the collection matrix, as illustrated in FIG. 4.

The assay reagents were prepared to for the performance of a cholesterol assay. The reagents necessary to measure plasma cholesterol were delivered in a unitized format referred to as a "unit dose reagent". The unit dose reagent is a delivery format in which the assay reagents are formed into a soluble mass. When contacted with the appropriate buffer, the unit dose reagent dissolves to release the component reagents without leaving behind insoluble materials which can interfere with the spectrophotometric determination of color.

The cholesterol assay unit dose reagent contained: cholesterol ester hydrolase (6660 units, Amano, Troy, Va.); cholesterol oxidase (940 units, Boehringer Mannheim Biochemicals, Indianapolis, Ind.); peroxidase (136,000 units, Amano); 4-aminoantipyrene (677 mg) and 3,5-dichlorohydroxybenzene sulfonate (2922 mg). The component reagents would react with the plasma sample to produce a red-colored reaction product, which can be read in a spectrophotometer (515 nm).

A reagent unit dose reagent was placed in a cuvette which was used as the sample receiver means of the diagnostic device, as described above and as depicted in FIGS. 4 and 5.

The assay was performed by placing a sample of whole blood (50 μL) on the top of the blood separator means. After about two minutes, the cell plasma separation was complete, leaving the collection matrix filled with plasma. The blood separator means was removed from the device, and plasma was eluted from the collection matrix into the cuvette by the addition of elution buffer (0.5 mL). The unit dose reagent dissolved upon the addition of plasma sample and buffer to the cuvette, thereby liberating the reagents necessary for the cholesterol assay. The absorbance of the resulting reaction mixture was read in a spectrophotometer.

The test was performed in duplicate using whole blood samples from 68 patients. The results of the assay were compared to assay results obtained with the Vision-Cholesterol Assay (Abbott Laboratories, Abbott Park, Ill.). The overall precision of the system, i.e., the blood separator, metering matrix and unit dose reagent, was calculated by averaging the coefficient of variation (%CV) of the individual determinations. The overall precision of the assay was determined to be 3.3%CV. The overall slope, intercept and correlation of each patient's cholesterol level determined by the present invention in comparison with the Vision assay determination were as follows: slope 0.93, intercept 14 and correlation 0.96. Therefore, the test device of the present invention provided acceptable precision and accuracy of assay results when correlated with the results of the reference method.

The concepts of the present invention are applicable to various types of assays and materials other than those specifically described herein. It will be appreciated that one skilled in the art can conceive of many other assays and materials to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A device for the measurement of a serum or plasma sample, comprising
   a) a matrix of sintered porous material of fixed dimensions, wherein said matrix is characterized by:
   i) a reproducible fluid uptake capacity proportional to the fixed dimensions of said matrix,
   ii) a minimal reactivity with plasma or serum components, and iii) a hydrophilic internal surface, thereby enabling said matrix to collect and retain a predetermined volume of sample for analysis; and b) a housing means whereby an entry port to said matrix is defined.

2. The device according to claim 1, wherein an exit port from said matrix is defined by said housing means.

3. The device according to claim 1, wherein said sintered porous material is selected from the group consisting of sintered glass, sintered steel, sintered ceramics and sintered plastics.

4. The device according to claim 1, wherein said sintered porous material is polyethylene.

5. The device according to claim 1, further comprising a blood separator means for separating plasma or serum from a whole blood sample, wherein said matrix is in liquid receiving relationship with said blood separator means, and wherein said matrix collects a predetermined volume of plasma or serum from said blood separator means.

6. The device according to claim 1, further comprising a sample receiver means, wherein said matrix transfers a predetermined volume of sample to said receiver means for analysis.

7. The device according to claim 6, wherein said sample receiver means is a reaction or detection vessel.

8. The device according to claim 7, wherein said sample receiver means is selected from the group consisting of a cuvette, a test tube, a slide and a reaction well.

9. The device according to claim 6, wherein said sample receiver means is an absorbant solid phase material having a pore size selected to induce the flow of sample from said matrix by capillary action.

10. The device according to claim 9, wherein said sample receiver means has a pore size smaller than the pore size of said matrix.

11. The device according to claim 1, further comprising an analytical reagent in said matrix, wherein said reagent is reconstituted upon the collection of test sample by said matrix.

12. The device according to claim 1, wherein said housing means has minimal reactivity with plasma or serum components.

13. The device according to claim 1, wherein said matrix is coated with dextran.

14. The device according to claim 1, wherein said matrix is coated with carboxylatex.

15. A device for the measurement of a serum or plasma sample, comprising a) a matrix of sintered porous material of fixed dimensions, wherein said sintered porous material is selected from the group consisting of sintered glass, sintered steel, sintered ceramics and sintered plastics, and wherein said matrix is characterized by:
  i) a reproducible fluid uptake capacity proportional to the fixed dimensions of said matrix,
  ii) a minimal reactivity with plasma or serum components, and
  iii) a hydrophilic internal surface, thereby enabling said matrix to collect and retain a predetermined volume of sample for analysis; and b) a housing means whereby an entry port to said matrix and an exit port from said matrix is defined.

16. The device according to claim 15, further comprising a blood separator means for separating plasma or serum from a whole blood sample, wherein said matrix is in liquid receiving relationship with said blood separator means, and wherein said matrix collects a predetermined volume of plasma or serum from said blood separator means.

17. The device according to claim 15, further comprising a sample receiver means, wherein said matrix transfers a predetermined volume of sample to said receiver means for analysis.

18. A method for collecting a serum or plasma sample for analysis, comprising:

a) providing a matrix of sintered porous material of fixed dimensions, wherein said matrix is characterized by:
  i) a reproducible fluid uptake capacity proportional to the fixed dimensions of said matrix,
  ii) a minimal reactivity with plasma or serum components, and
  iii) a hydrophilic internal surface, thereby enabling said matrix to collect and retain a predetermined volume of sample for analysis; and a housing means whereby an entry port to said matrix is defined;

b) applying a quantity of serum or plasma to said matrix; and c) collecting a predetermined volume of plasma or serum in said matrix.

19. The method according to claim 18, wherein said sintered porous material is selected from the group consisting of sintered glass, sintered steel, sintered ceramics and sintered plastics.

20. The method according to claim 18, wherein said sintered porous material is polyethylene.

* * * * *

UNITED STATES PATENT AND TRADEMARK OFFICE
CERTIFICATE OF CORRECTION

PATENT NO. : 5,064,541

DATED : Nov. 12, 1991

INVENTOR(S) : Tzyy-Wen Jeng, Kristin D. Elmore, Gary M. Oosta, Terry A. Pry

It is certified that error appears in the above-identified patent and that said Letters Patent is hereby corrected as shown below:

Column 7, line 23
Delete "co owned" and insert--co-owned--

Column 8, line 50
Delete "flow through" and insert--flow-through--

Column 9, line 48
Delete "1 um" and insert--10 um--

Column 15, line 25
Delete "co pending" and insert--co-pending--

Column 16, line 36
Delete "anti red" and insert--anti-red--

Signed and Sealed this

Twenty-fourth Day of August, 1993

Attest:

BRUCE LEHMAN

Attesting Officer    Commissioner of Patents and Trademarks